United States Patent
Baumgartner et al.

(10) Patent No.: US 10,716,945 B2
(45) Date of Patent: Jul. 21, 2020

(54) EXTERNAL UNIT FOR AN IMPLANTABLE NEURO STIMULATOR SYSTEM

(71) Applicant: MED-EL Elektromedizinische Geraete GmbH, Innsbruck (AT)

(72) Inventors: Josef Baumgartner, Ranggen (AT); Martin Zimmerling, Patsch (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 138 days.

(21) Appl. No.: 15/579,319

(22) PCT Filed: Jun. 17, 2016

(86) PCT No.: PCT/US2016/037978
§ 371 (c)(1),
(2) Date: Dec. 4, 2017

(87) PCT Pub. No.: WO2016/205589
PCT Pub. Date: Dec. 22, 2016

(65) Prior Publication Data
US 2018/0296845 A1    Oct. 18, 2018

Related U.S. Application Data (60) Provisional application No. 62/181,822, filed on Jun. 19, 2015.

(51) Int. Cl.
*A61N 1/372* (2006.01)
*A61N 1/02* (2006.01)
(Continued)

(52) U.S. Cl.
CPC ......... *A61N 1/37223* (2013.01); *A61N 1/025* (2013.01); *A61N 1/3787* (2013.01);
(Continued)

(58) Field of Classification Search
CPC ..................................................... H02J 50/20
See application file for complete search history.

(56) References Cited

U.S. PATENT DOCUMENTS 5,569,307 A    10/1996  Schulman et al.
6,321,118 B1   11/2001  Hahn
(Continued)

FOREIGN PATENT DOCUMENTS

| CN | 1897471 A   | 1/2007 |
| CN | 102006907 A | 4/2011 |

(Continued)

OTHER PUBLICATIONS

International Searching Authority, International Search Report—International Application No. PCT/US16/37978, dated Dec. 1, 2016 together with the Written Opinion of the International Searching Authority, 23 pages.

(Continued)

*Primary Examiner* — Scott Luan
(74) *Attorney, Agent, or Firm* — Sunstein LLP (57) ABSTRACT

An external unit for an implantable neuro stimulator system and a method of operating the same, comprising an external coil inductively couplable to an implant coil of an implantable neural stimulator unit when in close proximity to each other. An RF-signal generating module for generating and outputting an RF-signal to the coil for inductive power and/or data transfer to the implantable neural stimulator unit, a measurement unit connected to the coil for measurement of an electrical parameter at the coil and a controller connected to the measurement unit and comprising a comparator and a storage for storing the electrical parameter. The controller is configured to operate at least in normal operating and corrective action mode, and when in the normal operating mode, to repeatedly measure the electrical parameter with the measurement unit, determine with the com- (Continued)

parator a change of the measured electrical parameter in relation to the stored electrical parameter switch the controller into a corrective action mode when the change exceeds a threshold; and otherwise modify the stored electrical parameter by the measured electrical parameter.

12 Claims, 5 Drawing Sheets

(51) Int. Cl.
*A61N 1/378* (2006.01)
*H02J 50/12* (2016.01)
*H02J 50/20* (2016.01)
*H02J 50/90* (2016.01)
*A61N 1/36* (2006.01)
*A61N 1/362* (2006.01)

(52) U.S. Cl.
CPC .......... *A61N 1/37235* (2013.01); *H02J 50/12* (2016.02); *H02J 50/20* (2016.02); *H02J 50/90* (2016.02); *A61N 1/362* (2013.01); *A61N 1/3605* (2013.01); *A61N 1/3611* (2013.01); *A61N 1/36038* (2017.08)

(56) References Cited

U.S. PATENT DOCUMENTS

| | | |
|---|---|---|
| 8,315,706 B2 | 11/2012 | Single |
| 2005/0143786 A1* | 6/2005 | Boveja ............... A61N 1/36025 607/45 |
| 2009/0299437 A1 | 12/2009 | Zimmerling |
| 2010/0045480 A1 | 2/2010 | Vallapureddy et al. |
| 2010/0137948 A1 | 6/2010 | Aghassian et al. |
| 2012/0059435 A1 | 3/2012 | Daly |
| 2013/0085537 A1 | 4/2013 | Mashiach |
| 2013/0184785 A1 | 7/2013 | Aghassian |
| 2013/0257168 A1 | 10/2013 | Singh |
| 2014/0039579 A1* | 2/2014 | Mashiach ............ A61N 1/0551 607/61 |

FOREIGN PATENT DOCUMENTS

| | | |
|---|---|---|
| CN | 104001264 A | 8/2014 |
| WO | WO 2013/109770 | 7/2013 |

OTHER PUBLICATIONS

European Patent Office, Extended European Search Report, Application No. 16812486.5, dated Jun. 26, 2018, 10 pages.
China National Intellectual Property Administration, Office Action, Application No. 201680035574.X, dated Apr. 14, 2020, 8 pages.

* cited by examiner

EXTERNAL UNIT FOR AN IMPLANTABLE NEURO STIMULATOR SYSTEM

This application is a National Phase Entry of Patent Cooperation Treaty Application PCT/US2016/037978, filed Jun. 17, 2016, which in turn claims priority from U.S. Provisional Patent Application 62/181,822, filed Jun. 19, 2015, both of which are incorporated herein by reference in their entireties.

FIELD OF THE INVENTION

This invention relates to an implantable neuro stimulation system, to an external audio processor unit for a cochlear implant system, a vestibular prosthesis, a laryngeal or heart-rate pacemaker or any other implantable neuro stimulation system and a method of operating the same.

BACKGROUND ART

Neuro stimulation systems are widely used for substituting or supporting functions of the human body. Typically, these systems comprise an external, body worn, unit and an implantable neuro stimulator unit implanted under the skin of a patient. The external unit may communicate and transfer power transcutaneously to the implantable neuro stimulator unit via an RF-signal over inductive coupled coils. The coils are in close proximity to each other with usually only the skin of the patient in between and aligned to each other for example with a magnet in the center of the coil. The implantable neuro stimulator unit may communicate via load modulation with the external unit, known as back-telemetry. Such a neuro stimulation system may for example be a cochlear implant system for stimulation of the auditory nerve of a deaf person. Other examples include, but are not limited to, a vestibular prosthesis and a laryngeal or heart rate pacemaker.

U.S. Pat. No. 8,315,706 discloses a cochlear implant and method to place the external audio processor into a power down mode when no implantable unit is detected to reduce power consumption. The presence may be detected by either missing back-telemetry signaling from the implant or from reflected impedance by measuring the current used by the external audio processor to drive the coil for communication and power transfer to the implantable unit. This application is mute about further specifics.

U.S. Pat. No. 6,321,118 discloses a cochlear implant device and method to indicate a working inductive coupling between the external audio processor and the implantable unit. The external audio processor has a pair of directive couplers where one measures the forward and one reflected power at the coil. The inductive coupling is detected to be working when the ratio of forward to backward voltage exceeds a certain threshold. In addition a message is sent from the external audio processor to the implant and awaiting a response as handshake. This cochlear implant and method has the disadvantage that the circuitry needs additional expensive components increasing the cost and power drain.

U.S. Pat. No. 5,569,307 discloses an implantable cochlear stimulator having a back telemetry functionality for communication of data and status signals from the implantable stimulator unit to the external audio processor unit. A back-telemetry signal is transmitted from the implantable stimulator unit only when a combination of status signals within the implantable stimulator unit is fulfilled. The back-telemetry signal, when received at the audio processor unit, is used as a handshake signal to indicate to the audio processor unit that the implantable stimulator unit is in proper signal communication with the implantable stimulator unit and that normal operation can proceed. Such a mechanism has the disadvantage that the data transmission from the audio processor unit to the implantable stimulator unit has to be interrupted periodically during this handshake signaling. In one aspect, this may lead to audio signal drop outs or a need for increased data transmission bandwidth over the inductive link with increased power drain.

It is therefore an object of the present invention to provide an implantable neuro stimulation system that allows reliable and fast detection of inductive coupling between the external unit and the implantable unit with minimal and additional cheap standard electronic components and lowest possible power drain. It is a further object of the invention to provide a fully backward compatible external unit with existing implanted neuro stimulation systems and without the need of interruption of data transmission.

SUMMARY OF THE INVENTION

Embodiments of the present invention are directed to an external unit for an implantable neuro stimulator system and a method of operating the same, comprising an external coil inductively couplable to an implant coil of an implantable neural stimulator unit when in close proximity to each other. An RF-signal generating module for generating and outputting an RF-signal to the coil for inductive power and/or data transfer to the implantable neural stimulator unit, a measurement unit connected to the coil for measurement of an electrical parameter at the coil and a controller connected to the measurement unit and comprising a comparator and a storage for storing the electrical parameter. The controller is configured to operate at least in normal operating and corrective action mode, and when in the normal operating mode, to repeatedly measure the electrical parameter with the measurement unit, determine with the comparator a change of the measured electrical parameter in relation to the stored electrical parameter switch the controller into a corrective action mode when the change exceeds a threshold; and otherwise modify the stored electrical parameter by the measured electrical parameter.

The controller may be further configured in corrective action mode to put at least part of the external unit into a low power mode. The controller may do so only after failure to obtain, in response to a sent command, a reply from the implantable neural stimulator unit. The electrical parameter may be a RF-signal amplitude. The threshold may be a function of the electrical parameter value. The function may be decreasing with increasing electric parameter value. The controller may be further configured to make the repetition time dependent on a function of the electrical parameter. The repetition time may be decreasing with increasing electric parameter value.

Embodiments of the present invention are also directed to a method of operating an external unit of a neuro stimulation system with an implantable neural stimulator, comprising the steps of: generating a RF-signal with a RF generator and output to a connected coil for inductive power and/or data transfer to the implantable neural stimulator, measuring with a measurement unit connected to the coil an electrical parameter at the coil, operating a controller comprising a comparator and a storage for storing the electrical parameter measured by the measurement unit and to repeatedly i. measure the electrical parameter with the measurement unit; ii. determine with the comparator a change of the measured electrical parameter in relation to the stored electrical parameter and iii. switch the controller into a corrective action mode when the change exceeds a threshold; and otherwise iv. modify the stored electrical parameter by the measured electrical parameter.

In corrective action mode the external unit may be put at least in part into a low power mode. The external unit may in corrective action mode only put into low power mode after failure to obtain an identifier from the implantable neural stimulator unit. The electrical parameter may be a RF-signal amplitude. The threshold may be a function of the stored electrical parameter. The function may be decreasing with increasing electric parameter.

Embodiments of the present invention may also be directed to a neuro stimulation system and a method of operating the same comprising an implantable neural stimulator unit and an external unit according and operating according to embodiments of the present invention.

DETAILED DESCRIPTION OF SPECIFIC EMBODIMENTS

Embodiments of the present invention are directed to providing a neuro stimulation system comprising an external unit with a coil and an in a patient implantable neuro stimulation unit for stimulation of target neural tissue with a coil that allows reliable and fast detection of an inductive coupling between the external unit and the implantable neuro stimulation unit and switching the external unit into a low power mode, where at least part of the external unit is disabled to conserve power consumption, when no inductive coupling is detected to conserve power. This is achieved with minimal additional cheap standard electronic components and lowest possible power drain required by the external unit and may further be fully backward compatible with existing implanted neuro-stimulation systems. A still further object is to continuously communicate, without the need of interruption, particularly the data transmission from the external unit to the implantable neuro stimulator unit.

Figure 1A:
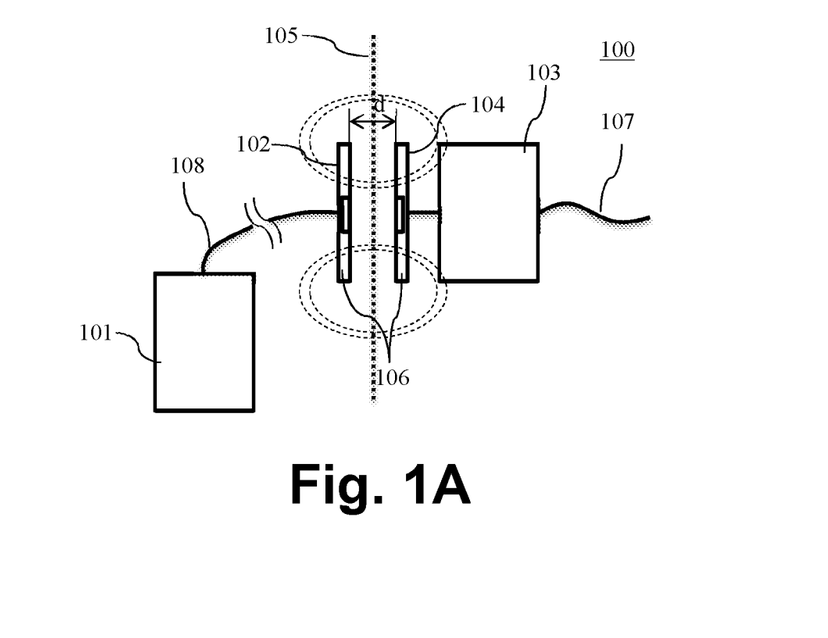
FIG. 1A schematically shows an implantable neural stimulator unit inductive coupled to an external wearable unit.
Figure 1B:
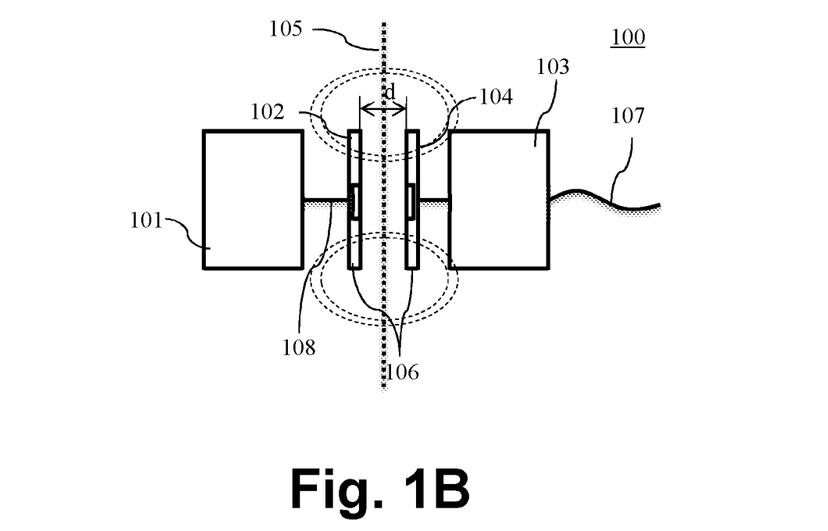
FIG. 1B schematically shows an implantable neural stimulator unit inductive coupled to an external behind-the-ear (BTE) audio processor.

Referring now to FIG. 1A of the drawings. Shown is a prior art implantable neuro stimulation system 100 comprising an external unit 101 with a coil unit 102 and an implantable unit 103 with a coil unit 104 implanted under the skin 105 of a patient. The implantable unit 103 may comprise an electrode 107 for stimulation of target neural tissue. The coil units 102 and 104 are aligned to each other, for example with a magnet 106 in the center of each coil and separated usually only with the thickness d of the skin 105 of the patient. The separation distance d is in the range of some millimetres, typically 8 mm, and may be up to 20 mm or in rare cases even more. This way both coil units 103 and 104 are inductive coupled, i.e. applying an RF-signal to coil unit 102 by the external unit 101 induces an RF-current in coil unit 104 of the implantable unit. The external unit 101 may be connected via cable 108 to the coil unit 102. This is the case for a body-worn external unit 101. For example for cochlear implants, infants may use body-worn audio processors. In another example and as shown in FIG. 1B, the external unit may be a head worn unit, such as for example a behind-the-ear audio processor for a cochlear implant. In a further example, the external unit 101 and the coil unit 102 may form one single unit (not shown). In this case no cable 108 is necessary to connect the external unit 101 and coil unit 102.

Figure 2:
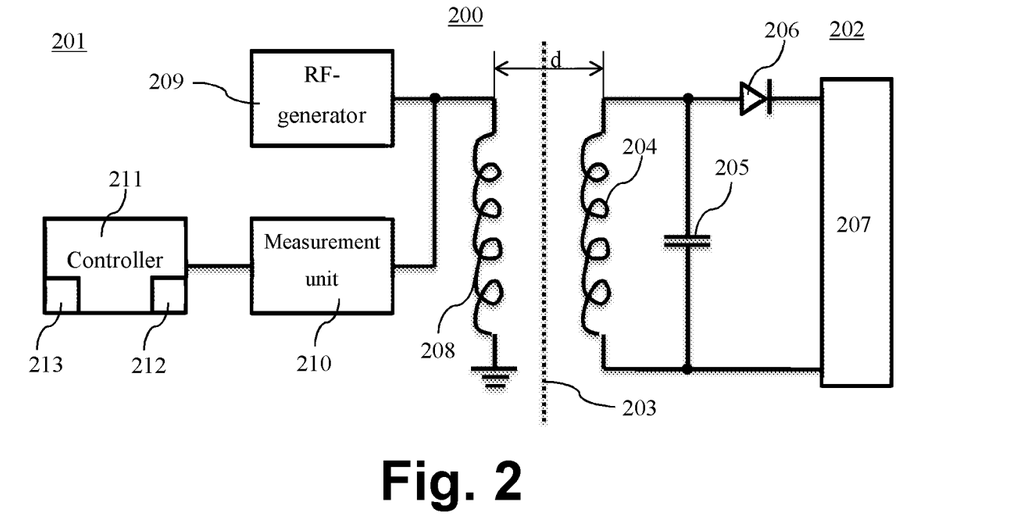
FIG. 2 schematically shows a neural stimulator system with an external unit, in accordance with an embodiment of the invention.

FIG. 2 schematically shows a neural stimulator system 200 with an external unit 201 and implantable neural stimulator unit 202 implanted under the skin 203 of a patient. The implantable unit comprises a coil 204 and capacitor 205 forming a parallel resonance circuit and having a resonance frequency matching with the RF-signal generated by the external unit 201. The received RF-signal with coil 204 is rectified by rectifier 206 and provided to power the implantable neural stimulator controller 207 comprising the stimulator electronic circuitries. The external unit 201 comprises a coil 208, a RF generating module 209 connected to the coil 208 for generating and output a RF-signal to the coil 208 for inductive power and/or data transfer to the implantable neural stimulator unit 202 during normal operation mode. The RF-signal is for example a 12MHz sinusoidal carrier signal modulated by the data signal. The RF generating module 209 in one embodiment may comprise a matching network for matching the impedance of the coil 208. The external unit 201 may further comprise a measurement unit 210 connected to the coil 208 for measurement of an electrical parameter at the coil 208 and a controller 211 connected to the measurement unit 201 comprising a comparator 212 and a storage 213 for storing the electrical parameter measured by the measurement unit 210. It is understood, that RF generating module 209, measurement unit 201 and controller 211 may be equally located in either external unit 101 or coil unit 102 without departing from the spirit of the invention. The controller 211 may be configured to repeatedly measure the electrical parameter with the measurement unit 210, determine with the comparator 212 a change of the electrical parameter in relation to the stored electrical parameter and switch the controller 211 into a corrective action mode when the change exceeds a threshold and otherwise modify the stored electrical parameter by the measured electrical parameter. Modification may include, without limitation, replacing with or low-pass filtering the measured electrical parameter. The low-pass filter may for example be a first-order, unity gain digital low-pass filter:

$$P_{stored,modified} = (1-a) \times P_{stored} + a \times P_{measured}$$

Where $P_{stored,modified}$ is the modified electrical parameter, $P_{stored}$ is the (former) stored electrical parameter, $P_{measured}$ is the measured electrical parameter and a the filter coefficition.

During normal operation mode, the RF generating module 209 generates a 12 MHz sinusoidal RF-signal, a so called carrier signal for output to coil 208. This carrier signal may be modulated with the data signal to be transmitted from the external unit 201 via coil 208 to the inductive coupled implantable neural stimulator unit 202. Various known types of modulations may be used and may without limitation include on-off keying, amplitude shift keying or frequency shift keying. The RF-signal may, due to inductive coupling induce a current in coil 204 of the implantable neural stimulator unit 202. Besides using the received and rectified signal to power the implantable unit 202, the implantable unit 202 may comprise, for example as part of the controller 207, a data extractor (not shown) for demodulating from the received signal the data signal. Such a data extractor is known in the art. The received and demodulated data signal may be used by controller 207 to generate the stimulation signal to be delivered by the electrode 107 to neural target tissue of an implanted patient. The measurement unit 209 may measure the electrical parameter at any time, for example periodic or upon request from the controller 211. The controller 211 may compare with comparator 212 the measured electrical parameter with the stored electrical parameter. The stored electrical parameter may be determined for example during an initialization phase, as described with reference to FIG. 5 below, and/or may be an electrical parameter of a former measurement.

The data signal may contain command signals to switch for example the implantable neural stimulator unit 202 into a certain operating mode or to respond with certain information. For example, the external unit 201 may send a command to the implantable neural stimulator 202 to provide an identifier, such as for example a device unique serial number or a status indicator. Upon reception of the command, the implantable neural stimulator 202 may, via for example load modulated back-telemetry, transmit its identifier to the external unit 201, that may decode the information by a data extractor. During such an operation, any continuous data delivery from the external unit 201 to the implantable neural stimulator 202 may be suspended for this period. This may lead to stimulation breaks and unwanted patient misperceptions, such as for example audio signal outages for cochlear implants or pain in case of laryngeal pacemakers.

Figure 3:
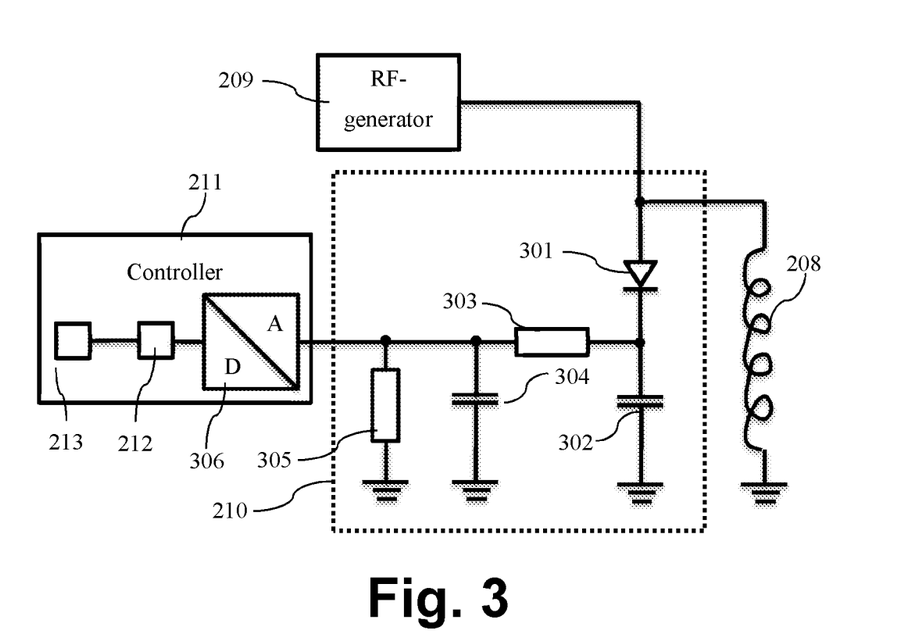
FIG. 3 schematically shows a part of an external unit, in accordance with an embodiment of the invention.

FIG. 3 schematically shows a part of an external unit 201 in accordance with one embodiment of the invention. Coil 208 is connected with RF generating module 209 and measurement unit 210. In one exemplary embodiment, the measurement unit 210 may comprise a rectifier 301 connected in forward direction to coil 208 to provide a rectified RF-signal to capacitor 302. The signal at capacitor 302 is further provided to a low-pass filter circuit comprising resistor 303, resistor 305 and capacitor 304 and for output to analog-to-digital converter 306. The low-pass filter circuit may be dimensioned, such that the measured electrical parameter corresponds to the RF-signal amplitude, i.e. follows the RF-signal amplitude, but may not be affected by the applied modulation. The analog-to-digital-converter 306 may be, as shown, part of the controller 211, but may also be part of the measurement unit 210. The measurement may be taken any time during normal operation, i.e. while RF generating module 209 is enabled and generates and outputs the RF-signal to coil 208. Advantageously, no extra communication to and from the implantable unit 202 is necessary and no interruption of data transmission is required.

Figure 4:
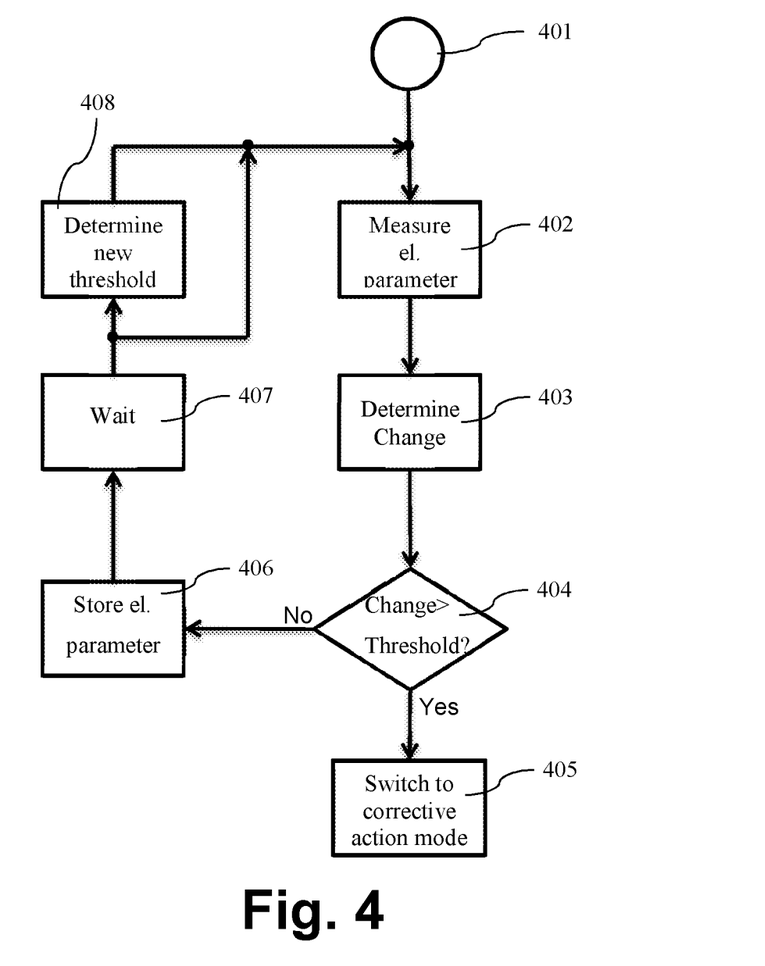
FIG. 4 shows a flow chart of the operation of the external unit, in accordance with an embodiment of the invention.

Reference is now made to FIG. 4, which shows a flow chart of the operation of the external unit, in accordance with an embodiment of the invention. The controller 211 starts a step 401 and first, at step 401, measures the electrical parameter with measurement unit 210 at the coil 208. In one embodiment the measurement may be carried out with a circuit as shown in FIG. 3. In still another embodiment, the electrical parameter may be the RF-signal amplitude. Next in step 403 the change of the measured electrical parameter in relation to the stored electrical parameter is determined with comparator 212, for example by subtracting the measured from the stored electrical parameter. At step 404 a check is performed as to whether the change exceeds a threshold and if so proceed to step 405 and otherwise proceed to step 406. The threshold may be pre-programmed in controller 211 or may in one embodiment be determined based on the measured electrical parameter. In step 405, the controller 211 is switched into a corrective action mode, which will be explained in more detail below. In step 406 the in storage 213 stored electrical parameter is modified with the measured electrical parameter. For step 403 of the following change determination, comparator 212 carries out the comparison with this new stored electrical parameter. Next, at step 407, the controller 211 waits a pre-determined time, before initiating again a new measurement cycle starting with step 402. The pre-determined time may be a parameter and pre-programmed at device manufacturing or during a fitting session by the fitting-software itself or the audiologist. Or in an embodiment of the invention depend on the stored electrical parameter. Optionally, after step 407 and before step 402, the controller 211 may determine a new threshold for step 404. The threshold may be pre-programmed or based on the stored electrical parameter.

Figure 6:
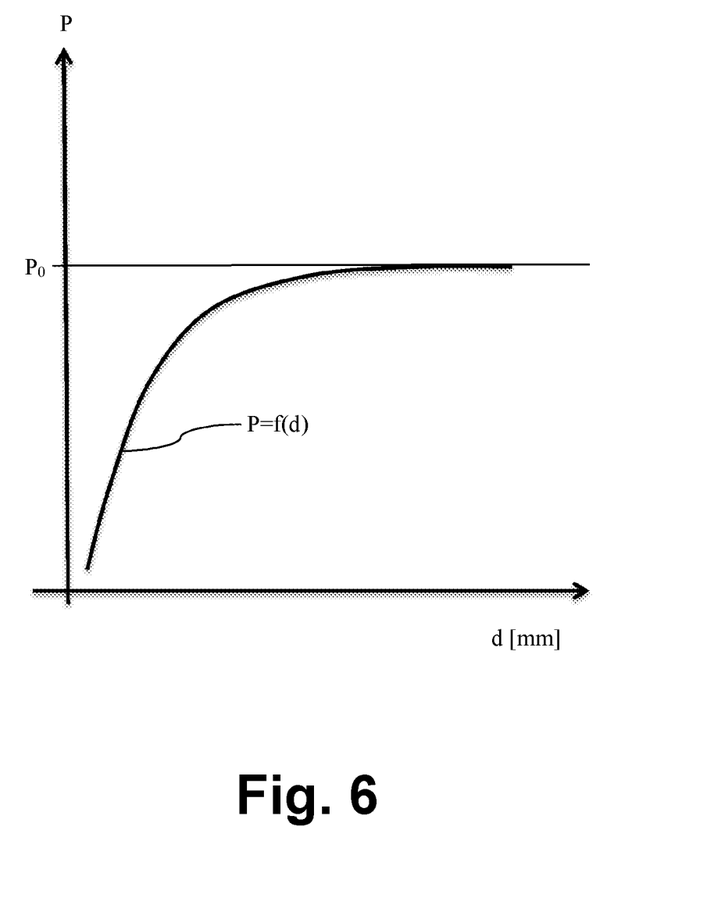
FIG. 6 depicts the dependency of the measured electrical parameter at the coil as a function of the distance f(d).

Determining the time the controller 211 waits before initiating again a new measurement cycle and/or determining the threshold dependent on the measured or stored electrical parameter may be explained in more detail in the following with reference to FIG. 6. In FIG. 6 is schematically the dependency of the measured electrical parameter P at coil 208 as a function f(d) of distance d in millimeters to coil 204 as measured by measurement unit 210 depicted. The separation distance d may include any possible lateral displacement of the coils to each other. From this graph it can be seen, that with increasing distance d, the measured electrical parameter P increases asymptotically until an electrical parameter $P_0$, representing open loop operation, is reached. As a consequence, any determined change of the electrical parameter will become smaller as the distance d becomes larger, i.e. the electrical parameter P becomes larger. To still reliable detect relative movement of the coils to each other, the threshold and/or the waiting time may be a function of the electrical parameter. In one embodiment the threshold and/or waiting time may decrease with increasing electrical parameter P. In a further embodiment, the function may be inversely proportional to the electrical parameter, for example:

$$\text{Threshold} = a/(b + c \times P)$$

Where a, b and c represent pre-determined parameters obtained for example by empirical tests during development and the electrical parameter P. The electrical parameter P may be the stored electrical parameter or the measured electrical parameter. The same applies for the waiting time. The waiting time is chosen as large as possible to obtain the lowest power consumption with smallest possible threshold to most reliable detect movement. Choosing the threshold too low, results in erroneous and unwanted switching to corrective action mode. The threshold on the one hand side does depend on the waiting time, i.e. a longer waiting time may lead to a larger change and thus, the threshold may be chosen larger as well to avoid unwanted switching to corrective action mode. On the other hand, the threshold may not be chosen to large, because change detection due to low resolution may no longer be reliable possible. Advantageously, the best balance in accordance with one embodiment of the invention may be achieved by making waiting time and threshold dependent on the electrical parameter as described above.

Figure 5:
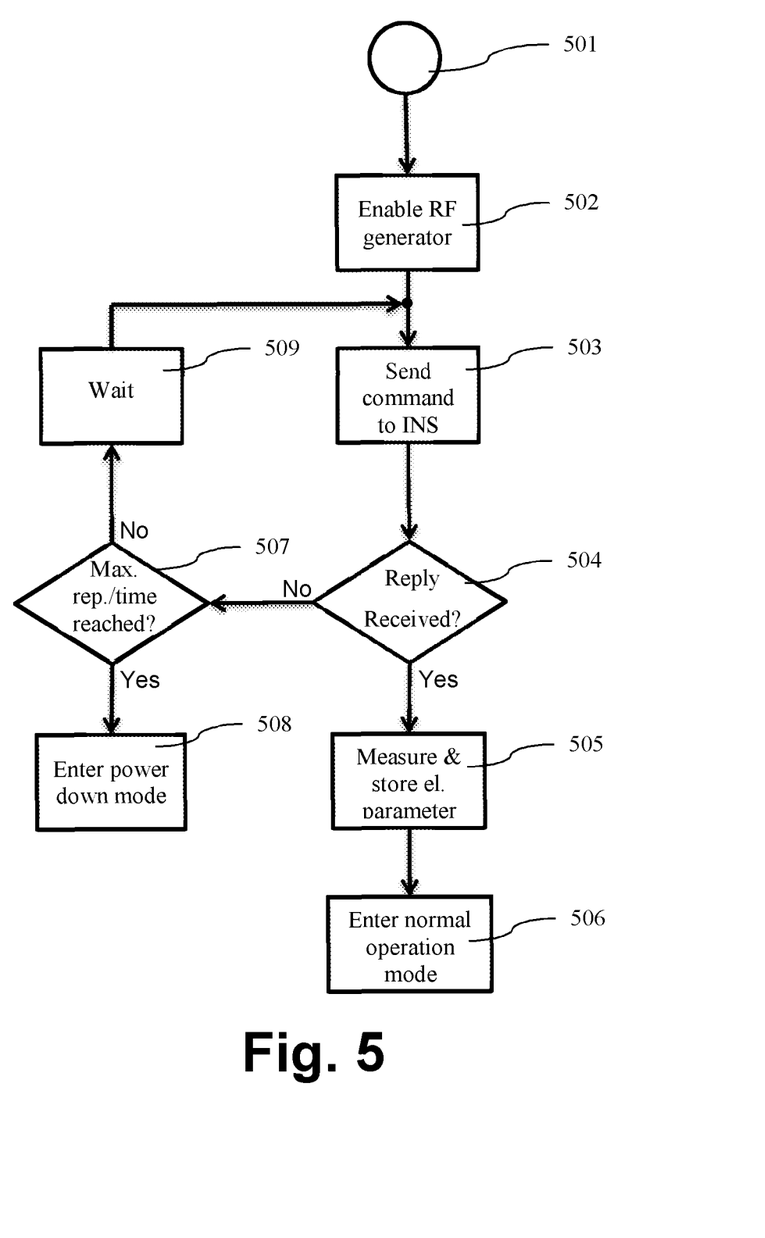
FIG. 5 shows a flow chart of the operation of the external unit in corrective action mode, in accordance with an embodiment of the invention.

FIG. 5 shows a flow chart of the operation of the external unit in corrective action mode, in accordance with an embodiment of the invention. Controller 211 starts from step 501 by for example powering on the external unit or switching to corrective action mode in step 405 as described before, and proceeds to step 502 where the RF-signal generating module 209 is enabled and outputs an RF-signal to coil 208. Step 502 is omitted when the RF-signal generating module 209 is already enabled. Next, at step 503, a command is sent to the implantable neural stimulator unit 202 (INS) as described before. At step 504 the external unit 201 checks for reception of a reply transmitted via back-telemetry from the implantable neural stimulator unit 202. The check may include a cyclic redundancy check (CRC) of the received data-word and/or a comparison with a pre-programmed device unique serial number. In case of a positive check, i.e. passing CRC and/or matching unique serial number with stored, controller 211 proceeds to step 505 where the electrical parameter is measured with the measurement unit 210 and stored in storage 213. Afterwards normal operation is started or resumed at step 506. This check ensures, that only when an implantable neural stimulator 202 is inductively coupled, and thus present, the controller 211 may proceed to normal operation and avoids otherwise erroneous implantable neural stimulator 202 detection due to the measurement only. This for example may occur when the coil 208 may be placed over a metallic plate.

In case the check at step 504 fails, controller 211 proceeds with step 507. The controller 211 checks whether a pre-determined time since first invocation of step 507 lapsed, or a pre-determined number of repetitions is reached. In both cases, the controller 211 proceeds to step 508 and puts at least a part of the external unit 201 into a low power mode. Otherwise, the controller 201 starts a new cycle with step 503 after waiting a pre-determined time. The external unit 201 may only wake from low power mode when powered on again. Alternatively, controller 211 may proceed after check at step 504 failed and omitting step 507, directly with step 509 and after waiting start a new measurement cycle with step 503. The controller 211 may stop only when the external unit 202 may be powered off. Setting the waiting time in step 509 to a few seconds, for example 3 to 5 seconds, the external unit 201 may stay most of the time in low power mode, but wakes up only for a measurement cycle every few seconds. In one embodiment, the waiting time in step 504 may be a couple milliseconds, for example 50 milliseconds, for a pre-determined number of cycles or time and afterwards set to some, for example 3 to 5, seconds. This way, the power consumption of the external unit 201 may be acceptable low, with the advantage that the external unit 201 automatically starts normal operation when the implantable unit 202 is detected.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments also can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Embodiments of the present invention may be implemented in various specific neuro stimulation systems, such as, without limitation, cochlear implant systems, totally implantable cochlear implant systems, vestibular implant systems, laryngeal pacemaker systems, middle ear implant systems and bone conduction implant systems. Although various exemplary embodiments of the invention have been disclosed, it should be apparent to those skilled in the art that various changes and modifications can be made which will achieve some of the advantages of the invention without departing from the true scope of the invention.

What is claimed is:

1. A neuro stimulation system comprising:
an implantable neural stimulator unit, for stimulation of target neural tissue, with a coil; and
an external unit comprising:
a coil inductively coupleable to the coil of the implantable neural stimulator unit when in close proximity to each other,
an RF-signal generating module configured for generating and outputting an RF-signal to the coil of the external unit for inductive power and/or data transfer to the implantable neural stimulator unit,
a measurement unit connected to the coil of the external unit and configured for measurement of an electrical parameter at the coil of the external unit, and
a controller connected to the measurement unit and comprising a comparator and a storage configured for storing the electrical parameter,
wherein the controller is configured to operate in (1) normal operating mode, (2) corrective action mode, and (3) low power mode, and when in the normal operating mode, to repeatedly:

i. measure the electrical parameter with the measurement unit;
ii. determine with the comparator a change of the measured electrical parameter in relation to the stored electrical parameter;
iii. switch the controller from the normal operating mode into the corrective action mode when the change exceeds a threshold, wherein the threshold relates to detection of inductive coupling between the external unit and the implantable neural stimulator unit; and otherwise
iv. modify the stored electrical parameter by the measured electrical parameter; and when in the corrective action mode, the controller is configured to put at least part of the external unit into the low power mode in response to sending a command and failing to obtain a reply from the implantable neural stimulator unit.

2. A neuro stimulation system according to claim 1 wherein the electrical parameter is the RF-signal amplitude.

3. A neuro stimulation system according to claim 1 wherein the threshold is a function of the electrical parameter value.

4. A neuro stimulation system according to claim 3 wherein the function is decreasing with increasing electric parameter value.

5. A neuro stimulation system according to claim 1 wherein the controller is further configured to make the repetition time dependent on a function of the electrical parameter.

6. A neuro stimulation system according to claim 5 wherein the repetition time decreases with increasing electric parameter value.

7. A neuro stimulation system according to claim 1, wherein the controller is further configured to repeatedly:
v. determine a new value for the threshold, as a function of the stored electrical parameter, such that the new value relates to a change in distance between the external unit and the implantable neural stimulator unit.

8. A method of operating a neuro stimulation system with an implantable neural stimulator unit, for stimulation of target neural tissue, with a coil, and an external unit, the method comprising:

a. generating an RF-signal with an RF generator and outputting to a connected coil of the external unit for inductive power and/or data transfer to the implantable neural stimulator
b. measuring with a measurement unit connected to the coil of the external unit, an electrical parameter at the coil of the external unit;
c. operating a controller, comprising a comparator and a storage for storing the electrical parameter measured by the measurement unit, in (1) normal operating mode, (2) corrective action mode, and (3) low power mode, and when in the normal operating mode repeatedly:
i. measure the electrical parameter with the measurement unit;
ii. determine with the comparator a change of the measured electrical parameter in relation to the stored electrical parameter;
iii. switch the controller from the normal operating mode into the corrective action mode when the change exceeds a threshold, wherein the threshold relates to detection of inductive coupling between the external unit and the implantable neural stimulator unit; and otherwise
iv. modify the stored electrical parameter by the measured electrical parameter; and when in the corrective action mode, operating the controller to put, at least in part, the external unit into the low power mode in response to sending a command and failing to obtain an identifier from the implantable neural stimulator unit.

9. A method according to claim 8, wherein the electrical parameter is a RF-signal amplitude.

10. A method according to claim 8, wherein the threshold is a function of the stored electrical parameter.

11. A method according to claim 10, wherein the function is decreasing with increasing electric parameter.

12. A method according to claim 8, wherein when in the normal operating mode also repeatedly:
v. determine a new value for the threshold, as a function of the stored electrical parameter, such that the new value relates to a change in distance between the external unit and the implantable neural stimulator unit.

\* \* \* \* \*